US008187248B2

(12) United States Patent
Zihlmann

(10) Patent No.: US 8,187,248 B2
(45) **Date of Patent: *May 29, 2012**

(54) SYSTEM AND DEVICE FOR REMOVING PHARMACEUTICAL PRODUCTS

(75) Inventor: Rudolf Zihlmann, Langnau (CH)

(73) Assignee: Roche Diagnostics International AG, Steinhausen (CH)

( * ) Notice: Subject to any disclaimer, the term of this patent is extended or adjusted under 35 U.S.C. 154(b) by 640 days.

This patent is subject to a terminal disclaimer.

(21) Appl. No.: 12/207,747

(22) Filed: Sep. 10, 2008

(65) Prior Publication Data

US 2009/0012492 A1 Jan. 8, 2009

Related U.S. Application Data

(63) Continuation of application No. 11/675,337, filed on Feb. 15, 2007, now Pat. No. 7,435,246.

(30) Foreign Application Priority Data

Feb. 16, 2006 (EP) .................................... 06003098

(51) Int. Cl.
*A61B 19/00* (2006.01)

(52) U.S. Cl. ......................... 604/403; 604/411; 604/414

(58) Field of Classification Search .................... 604/86, 604/186, 187, 256, 403, 407, 411, 412, 413, 604/414, 415, 416, 905; 141/312, 318, 319, 141/329, 390, 392; 222/153.01, 206, 498, 222/511, 522, 526, 540, 575
See application file for complete search history.

(56) References Cited

U.S. PATENT DOCUMENTS 3,023,925 A 3/1962 Sher
3,080,866 A 3/1963 Friedman
3,826,260 A * 7/1974 Killinger ....................... 604/413
4,775,363 A 10/1988 Sandsdalen
4,998,713 A 3/1991 Vaillancourt
5,032,114 A 7/1991 Olovson
5,094,148 A 3/1992 Haber et al.
5,460,617 A 10/1995 Minkus et al.
5,688,252 A 11/1997 Matsuda et al.
5,833,213 A * 11/1998 Ryan .......................... 251/149.1
5,890,610 A * 4/1999 Jansen et al. .................. 215/253

(Continued)

FOREIGN PATENT DOCUMENTS

DE 88 09 014 10/1988

(Continued)

OTHER PUBLICATIONS

Online dictionary entry for "ergonomic" accessed Aug. 24, 2007. http://www.askoxford.com/concise_oed/ergonomic?view=uk.

(Continued)

*Primary Examiner* — Leslie Deak
*Assistant Examiner* — Adam Marcetich
(74) *Attorney, Agent, or Firm* — Dinsmore & Shohl LLP

(57) ABSTRACT

A system for removing or transferring a pharmaceutical product from a reservoir including an ampoule with a moveable piston therein and an adaptor which includes, generally along a longitudinal axis, a reservoir connector and an ampoule connector for coupling to the ampoule, wherein the ampoule connector includes at least one locking mechanism which, in a side wall, includes a resilient element generally corresponding to a portion of the side wall which extends along the periphery thereof and, at opposing ends, merges with the side wall.

17 Claims, 4 Drawing Sheets

U.S. PATENT DOCUMENTS

| | | | | |
|---|---|---|---|---|
| 6,129,712 | A | 10/2000 | Sudo et al. | |
| 6,146,362 | A | 11/2000 | Turnbull et al. | |
| 6,159,192 | A * | 12/2000 | Fowles et al. | 604/403 |
| 6,280,430 | B1 | 8/2001 | Neftel et al. | |
| 6,402,207 | B1 | 6/2002 | Segal et al. | |
| 6,568,434 | B2 | 5/2003 | Zinger | |
| 6,729,370 | B2 * | 5/2004 | Norton et al. | 141/329 |
| 2002/0095121 | A1 | 7/2002 | Norton et al. | |
| 2002/0189705 | A1 | 12/2002 | Reihl et al. | |
| 2002/0189712 | A1 | 12/2002 | Safabash | |
| 2003/0070726 | A1 | 4/2003 | Andreasson et al. | |
| 2003/0199846 | A1 | 10/2003 | Fowles et al. | |
| 2004/0015148 | A1 * | 1/2004 | Curutcharry | 604/414 |
| 2004/0040965 | A1 | 3/2004 | Gehring et al. | |
| 2004/0112457 | A1 * | 6/2004 | Norton et al. | 141/26 |
| 2004/0249341 | A1 | 12/2004 | Newbrough et al. | |
| 2006/0184103 | A1 | 8/2006 | Paproski et al. | |
| 2007/0282278 | A1 * | 12/2007 | Knight | 604/236 |

FOREIGN PATENT DOCUMENTS

| | | |
|---|---|---|
| FR | 2853830 | 10/2004 |

OTHER PUBLICATIONS

European Office Action for 06 003 098.8 dated Apr. 21, 2008.

USPTO Final Office Action mailed Mar. 30, 2011 pertaining to co-pending U.S. Appl. No. 12/120,527, filed May 14, 2008.

USPTO non-final Office Action mailed Jul. 8, 2010 pertaining to co-pending U.S. Appl. No. 12/120,527, filed May 14, 2008.

USPTO Electrons/Restriction mailed Sep. 2, 2010 in reference to co-pending U.S. Appl. No. 12/120,527, filed May 14, 2008.

USPTO non-final Office Action dated Jun. 17, 2011 pertaining to co-pending U.S. Appl. No. 12/120,527.

* cited by examiner

SYSTEM AND DEVICE FOR REMOVING PHARMACEUTICAL PRODUCTS

CROSS-REFERENCE TO RELATED APPLICATION(S)

This application is a continuation of U.S. application Ser. No. 11/675,337, filed on Feb. 15, 2007, which claims priority to European Patent Application No. 06 003 098.8 filed Feb. 16, 2006, the content of which is incorporated in its entirety by reference herein.

BACKGROUND

The present invention relates to devices from administering, injecting, infusion, dispensing or delivering substances, and to methods of making and using such devices. More particularly, it relates to a system and a device for removing a pharmaceutical product or substance from a reservoir.

In medicine, primarily liquid pharmaceutical products or substances are often filled into sealed reservoirs or containers, for example into vials with a content of a few milliliters. Medical personnel, for example, may pierce the seal of the container with a cannula and fill a syringe with a required amount of pharmaceutical product, as required.

To avoid handling exposed cannulas, and the risk of injury associated therewith, adaptors may be used between the container and the syringe. Various embodiments of an adaptor are, for example, known from U.S. Pat. No. 6,591,876. This adaptor has a first container connector for coupling to a first container, a second container connector for coupling to a second container, a central part between the two connectors and a cannula which the central part keeps protected from inadvertent contact inside the adaptor. The first container connector has elements separated from one another by slots in the side wall thereof to enclose a part of the first container. The second container connector has two openings in the side wall thereof to receive on a front part of the second container two laterally projecting parts similar to a snap connection. In one embodiment, the adaptor has a locking mechanism, which holds the adaptor after coupling to the container in a position in which the central part is compressed. In a further embodiment, wherein this compression is not required, the central part is rigid and has two opposing grip surfaces.

In one application, an adaptor is used to fill an ampoule for an insulin pump, for example an Accu-Chek® insulin pump from Roche Diagnostics GmbH, Germany, with insulin. The insulin pump continuously dispenses insulin to the body, via a thin tube, the cannula thereof being located under the skin. Microprocessors control a motor which moves a stopper, for example every three minutes, via a threaded rod into an insulin ampoule. The patient may replace an empty ampoule either by an ampoule, which has been refilled with insulin by himself, or by an ampoule which is ready to use.

Devices for self-administering pharmaceutical products should to be able to be handled in a user-friendly manner, easily and without a great expenditure of force.

SUMMARY

An object of the present invention, therefore, is to provide a system and a device for removing or transferring a liquid pharmaceutical product from a container, so that the coupling between the adaptor and the ampoule and between the adaptor and the reservoir is possible in a user-friendly manner. To achieve this, in a device and system in accordance with the present invention, the device is designed such that it comprises at least one locking mechanism which comprises a resilient element.

One aspect of the present invention relates to a system for removing a pharmaceutical product from a reservoir. In one embodiment, the system comprises an ampoule in which a moveable piston is arranged and an adaptor which has a reservoir connector and an ampoule connector for coupling to the ampoule in a longitudinal direction. The ampoule connector has at least one locking mechanism which, in a side wall, comprises a resilient element. The resilient element corresponds to a portion of the side wall which extends along the periphery thereof and at opposing ends merges with the side wall.

In one embodiment the present invention comprises an adaptor having, in a longitudinal direction or extending longitudinally, a reservoir connector and an ampoule connector for coupling to an ampoule. The ampoule connector has at least one locking mechanism which, in a side wall, comprises a resilient element. The resilient element corresponds to a portion of the side wall which extends along the periphery thereof and at opposing ends merges with the side wall.

In one embodiment, the present invention comprises an adaptor for facilitating the transfer of a substance from one container to another, the adaptor comprising a reservoir connector for coupling to a reservoir and an ampoule connector for coupling to an ampoule, wherein the ampoule connector comprises a side wall with a peripheral area and a locking mechanism comprising a resilient element generally in the peripheral area and having opposing ends which merge with the side wall and a slot, the resilient element extending generally parallel to the slot. The reservoir connector comprises a side wall, at least one portion of the side wall producing a bulged portion on an inner face of the side wall. The adaptor further comprises a central part extending generally between the reservoir connector and the ampoule connector, the central part comprising two opposing openings through which a front part of the ampoule is visible and at least one rib element extending radially outwardly. In some embodiments of the present invention, the adaptor may be combined with an ampoule or container in which a moveable piston is housed, thereby providing a system for transferring a substance from a reservoir to the ampoule.

DETAILED DESCRIPTION

Various methods for implementing the present invention are disclosed hereinafter without restricting the scope of the invention, with reference to an exemplary embodiment of an insulin pump as an administering device. An insulin pump is, however, only one example of an application or use, in which in a preparatory step a pharmaceutical product, e.g. insulin for treating diabetes, is removed from a container to use it in a further container in an administering device. In further applications, growth hormones may be used for growth abnormalities, erythropoietin (EPO) may be used for kidney failure or general lack of red blood cells or α-interferon may be used in the treatment of hepatitis or cancer, as pharmaceutical products.

The various methods for implementing the present invention are, moreover, not restricted to liquid pharmaceutical products, although in medical applications these are frequently removed from a reservoir. The invention is, however, generally applicable to pharmaceutical products of variable viscosity (e.g. from liquid to powdery lyophilisate which has to be dissolved by liquid).

Figure 1:
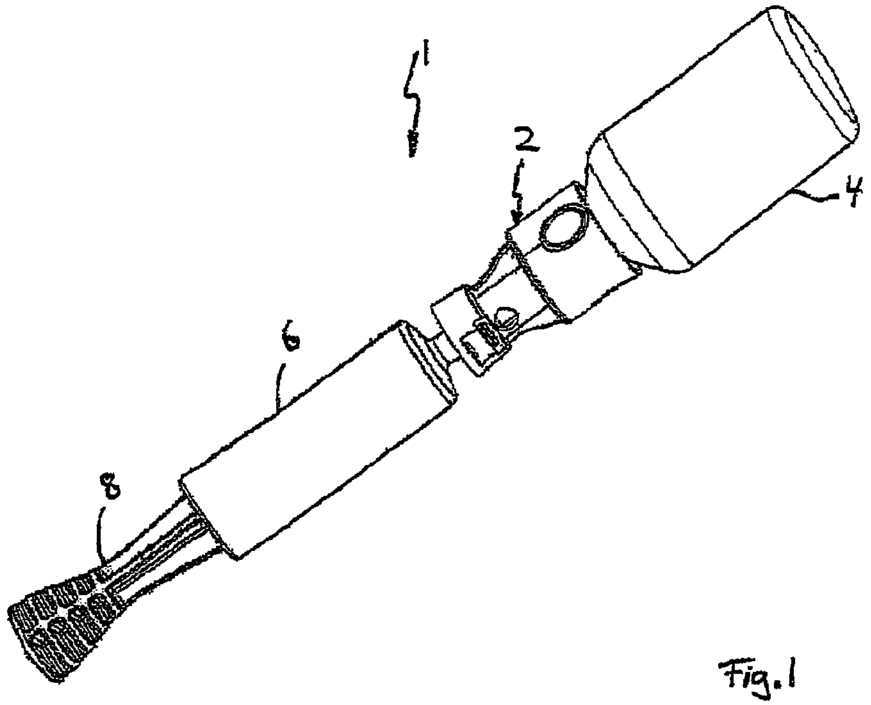
FIG. 1 is a schematic representation of an embodiment of a system in accordance with the present invention for removing a liquid pharmaceutical product.

FIG. 1 shows a schematic representation of an embodiment of a system 1 for removing a pharmaceutical product, for example a liquid pharmaceutical product, from a reservoir 4. The system 1 has an adaptor 2 and an ampoule 6 with a piston 8 which is movable therein. The terms "reservoir" and "ampoule" in this case generally denote a container which is suitable for receiving a substance. The reservoir 4 and the ampoule 6 may be made from a rigid or stiff material, such as for example plastics, glass, metal, or may be made from a material which is flexible or resilient, such as for example a film made from plastics or a different material.

By using the adaptor 2 the pharmaceutical product may be removed from the reservoir 4 and transferred into the ampoule 6. To remove the pharmaceutical product, the ampoule 6 and the reservoir 4 may be coupled to the adaptor 2. A connection between the inside of the reservoir 4 and the inside of the ampoule 6 is thereby created by a hollow needle or cannula. If, for example, a patient withdraws the piston 8 from the ampoule 6, the pharmaceutical product flows into the ampoule 6. The filled ampoule 6 may then, for example, be inserted into an insulin pump. In one embodiment, a piston rod is additionally removed from the piston 8, so that only one piston stopper remains in the ampoule 6 for sealing. The piston 8 is shown in more detail in FIGS. 5 and 6A-6D.

Figure 2:
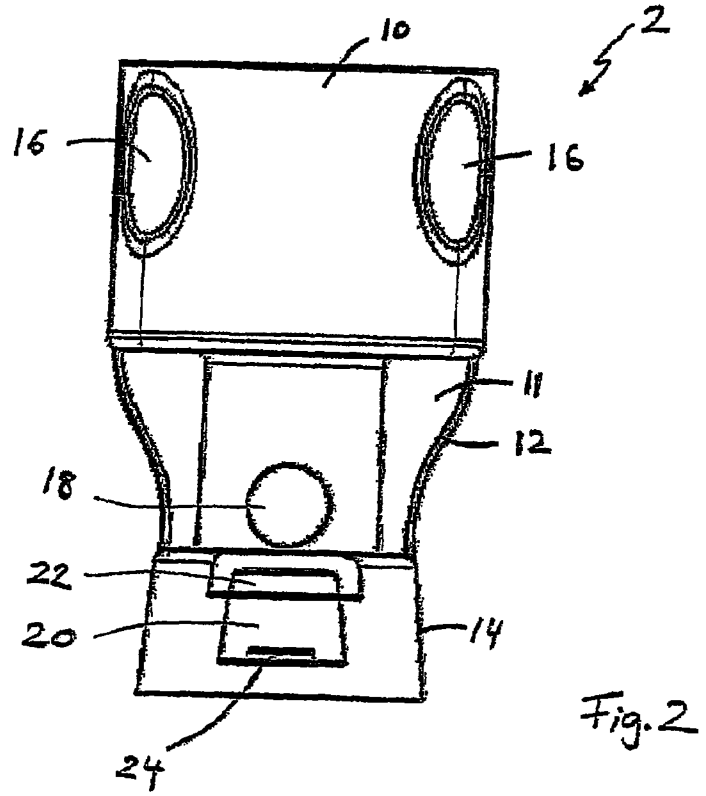
FIG. 2 is a side view of an embodiment of an adaptor in accordance with the present invention.
Figure 3:
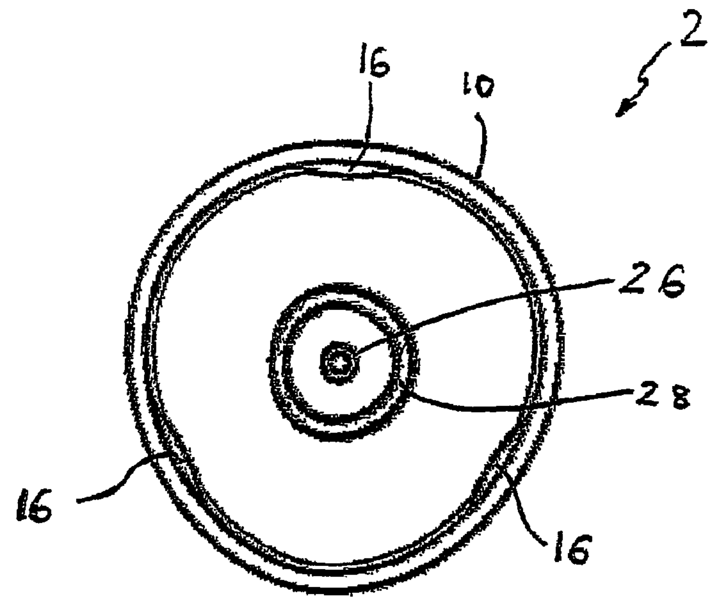
FIG. 3 is a plan view of the adaptor shown in FIG. 2.
Figure 4:
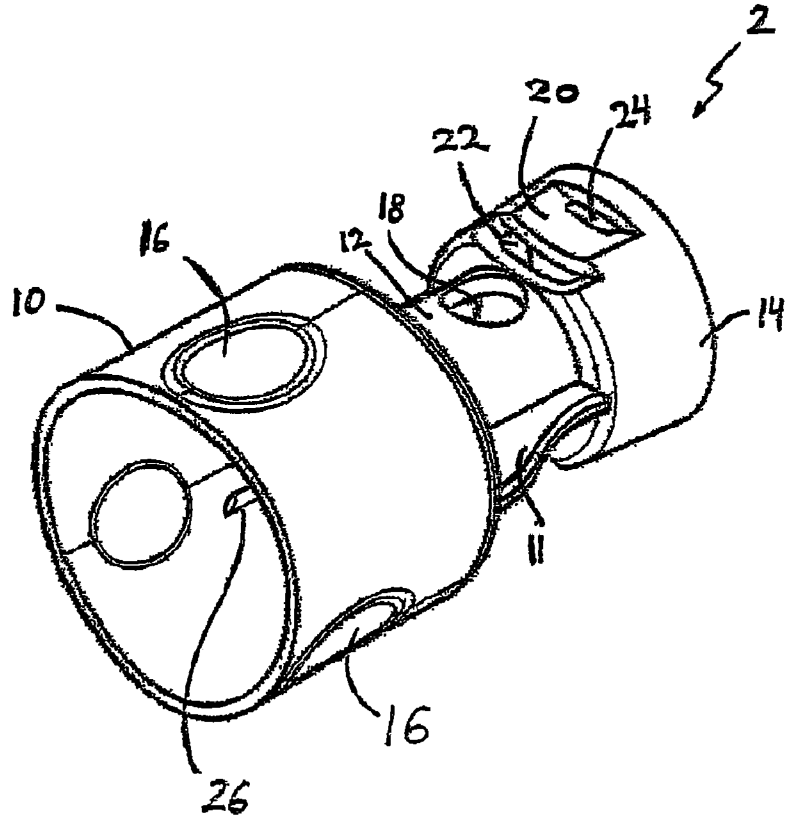
FIG. 4 is a perspective view of the adaptor shown in FIG. 2.

FIG. 2 shows a side view of an exemplary embodiment of the adaptor 2 in accordance with the present invention. The adaptor 2 has a reservoir connector 10, a central part 12 and an ampoule connector 14. The reservoir connector 10 is coupled to the reservoir 4 and has approximately the shape of a hollow cylinder, on the outer wall thereof, along the periphery, a plurality of recesses 16, for example three, being located. The recesses 16 produce bulged or outstanding portions or regions on the inner wall which are shown in FIGS. 3 and 4.

In the embodiment shown, the central part 12 has a cylindrical part which connects the reservoir connector 10 to the ampoule connector 14. The central part 12 has, moreover, one or more, for example two, ribs or rib elements 11, which project radially outwardly and extend outside the cylindrical part between the reservoir connector 10 and the ampoule connector 14. The ribs 11 facilitate the gripping and/or holding of the adaptor 2. In the embodiment shown, the central part 12 has in the vicinity of the ampoule connector 14 two opposing openings 18 through which, for example, the patient or user is able to see a front part of the ampoule 6 (for example one part of a Luer connector shown in FIG. 5), and thus also whether air or the pharmaceutical product is located in the front part. This makes it easier for the patient, at the end of the filling process, to remove undesired air in the known manner from the ampoule 6.

The ampoule connector 14 is coupled to the ampoule 6 and has approximately the shape of a hollow cylinder, the diameter thereof increasing outwardly, in the embodiment shown, from the central part 12. In the coupled state of the system the ampoule connector 14 receives a part of the Luer connector. In the embodiment shown, moreover, the ampoule connector 14 has in the outer wall thereof two opposing locking mechanisms, which respectively consist of two slots 22, 24 and a resilient element 20, which also may be referred to or thought of as a web 20. The slots 22, 24 respectively produce openings and the resilient element 20 may be resiliently deformable in the radial direction. The ampoule connector 14, in particular the locking mechanisms, are adapted to cooperate with or complement the front part of the ampoule 6 shown in FIG. 5 (for example in the form of a Luer connector).

In a further embodiment, instead of two slots 22, 24 only one slot may be present. In this embodiment, the resilient element 20 and the slot are part of a locking mechanism. Also in this embodiment, the resilient element 20 may be resiliently deformed in the radial direction.

FIG. 3 shows a plan view of the adaptor 2 shown in FIG. 2, so that the reservoir connector 10 and a hollow needle 26 or cannula 26 are visible. In the embodiment shown, the outer wall of the reservoir connector 10 has a shape deviating from a circle. In a further embodiment, the outer wall may have a different shape, for example, a circular shape. The shape shown in FIG. 3, deviating from a circle, is produced by flattening a circular outer wall in the region of the three recesses 16, for example by reshaping and/or by a suitable forming process. As shown in FIG. 3, the recesses 16 are equally distributed along or about the periphery of the outer wall and produce bulged portions or outstanding regions inside the reservoir connector 10. The non-circular shape allows reservoirs 4 which have slightly different diameters to be received. As the size of the reservoir 4 increases, the shape approaches an optimal circle. A difference between the non-circular shape and the shape of an optimal circle may be used as deformation for compensating for different diameters. The bulged portions are used to retain the reservoir 4 in the adaptor 2.

On the base of the reservoir connector 10 a circular bulged or outstanding portion 28 encloses the cannula 26. The diameter of the bulged portion 28 is adapted to the outer diameter of one end of the reservoir front part. The bulged portion 28 is used for the longitudinal compensation of different reservoirs 4, as the bulged portion 28 is able to enter the resilient septum (pierceable membrane).

Figure 5:
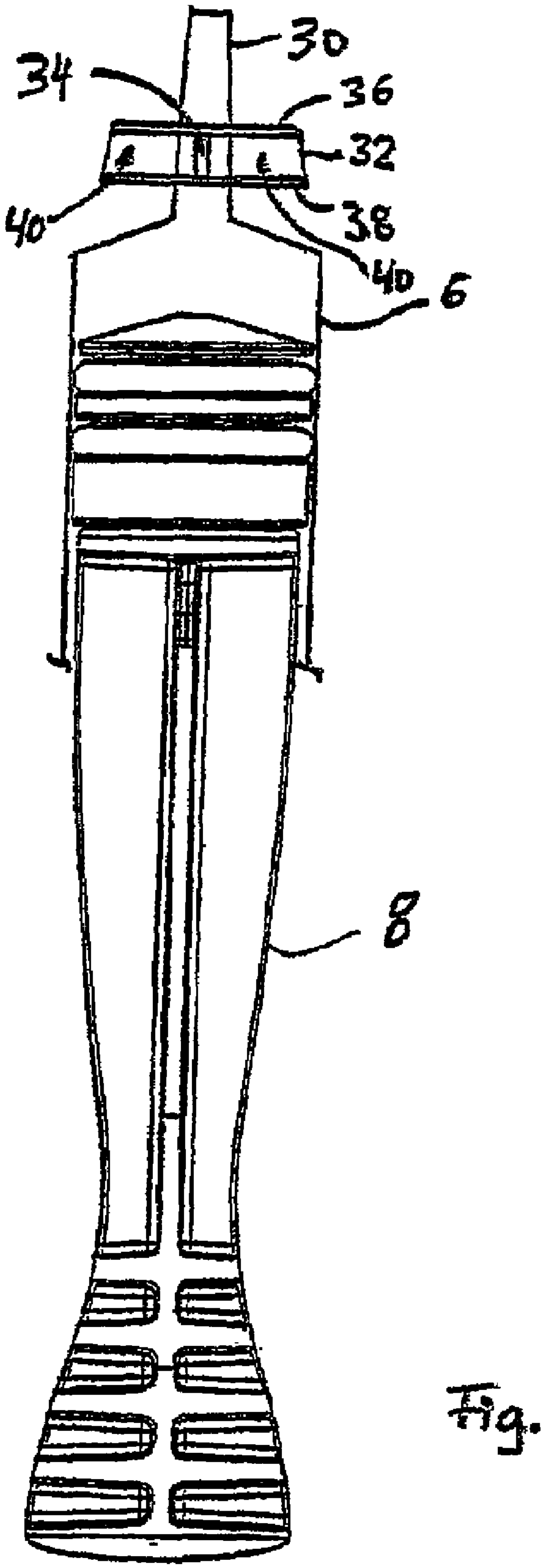
FIG. 5 is a schematic representation of a piston in an ampoule.

The mode of operation of the locking mechanism of the adaptor 2 is disclosed hereinafter with reference to FIGS. 4 and 5. FIG. 4 shows a perspective view of the adaptor 2 in which, amongst others, one of the three elements 11 and one of the two locking mechanisms are visible. FIG. 5 shows a schematic representation of the piston 8 arranged in the ampoule 6. The ampoule 6 is shown in FIG. 5 only in the front region thereof.

The web 20 corresponds to an elongate portion of the outer wall which extends along the periphery thereof and parallel to the slots 22, 24 and merges with the outer wall at its ends. In the direction of the central part 12, the slot 22 borders on one longitudinal side of the web 20 and, in the direction of the ampoule 6, the slot 24 borders on a further longitudinal side of the web 20. As indicated in FIG. 4, the web 20 may be curved into the inside of the ampoule connector 14. In one embodiment, the adaptor 2 is made from polypropylene (PP), which may be resiliently deformed. The web 20 is, therefore, also resilient, primarily in the radial direction.

In one embodiment, the front part of the ampoule 6 is based on a (male) Luer connector 30 which is provided with a collar part 32. The collar part 32 projects substantially perpendicularly from a longitudinal axis of the Luer connector 30. The collar part 32 has two circular parts 36, 38 which are separated from one another in the direction of the longitudinal axis by four braces 34. As a result, four hollow spaces 40 which are separated from one another are produced between the parts 36, 38.

For coupling the ampoule 6 to the adaptor 2, the front part of the ampoule 6 is pushed into the ampoule connector 14 and the ampoule 6 and the adaptor 2 are pressed against one another. The circular collar part 36 initially presses or urges the webs 20 outwardly. When the opposing webs 20 encounter hollow spaces 40, the two webs 20 noticeably engage in the corresponding hollow spaces 40. If the webs 20 thereby should encounter braces 34, the webs 20 may be positioned by slight axial rotation of the ampoule 6 and/or the adaptor 2 such that they encounter hollow spaces 40 and the webs 20 are able to engage. In the engaged state the circular collar part 36 penetrates the openings 22, and the webs 20 relax into their original state and thus ensure the coupling.

For decoupling, the patient may pull the ampoule 6 and the adaptor 2 apart, in some embodiments in association with an axial rotation of the ampoule 6 and/or the adaptor 2. During rotation, the braces 34 press, urge and/or flex the webs 20 outwardly, whereby the ampoule 6 and the adaptor 2 may be separated from one another with a relatively low expenditure of force.

Figure 6B:
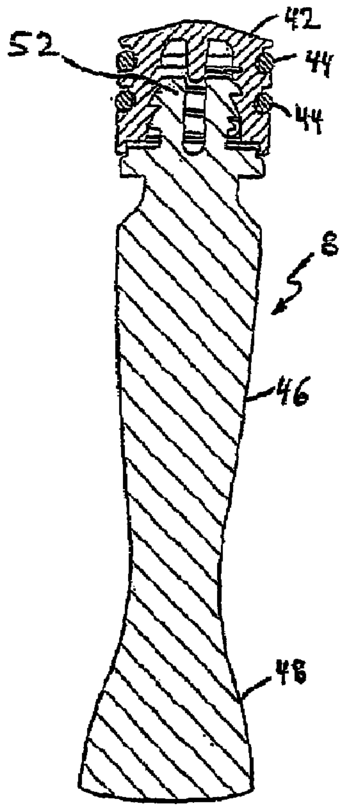
FIGS. 6A and 6B are schematic representations of a piston with a piston rod and a piston stopper.
Figure 6A:
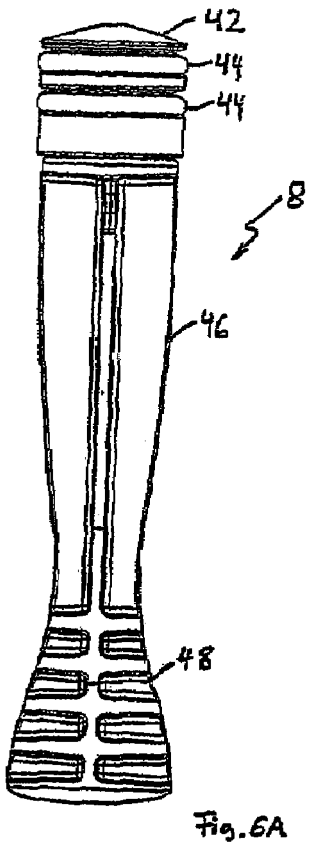

FIGS. 6A and 6B show schematic representations of the piston 8 which has a piston rod 46 and a piston stopper 42. FIG. 6B shows a longitudinal section through the piston 8. The piston stopper 42 is connected by being able to be screwed to a front end of the piston rod 46 and has two sealing rings 44. Each sealing ring 44 is located in a groove which extends along the periphery of the piston stopper 42. The front end of the piston rod 46 has a screw part 52 which is screwed into a blind hole of the piston stopper 42. The screw part 52 has a male thread which is adapted to a corresponding female thread of the blind hole.

At a rear end, the piston rod 46 has an ergonomically shaped grip 48, by which the patient is able to grip and pull the piston 8. The ergonomically shaped grip 48 is seamlessly adjoined to the remaining part of the piston rod 46. The grip 48 is generally designed such that the patient is able to grip it with two fingers (for example between the thumb and forefinger) or three fingers (for example with the thumb, forefinger and middle finger) in a comfortable and natural manner. In particular, it offers the patient a relatively large gripping surface. Edges which some patients may experience as unpleasant or even as painful are thus avoided as far as possible.

Figure 6D:
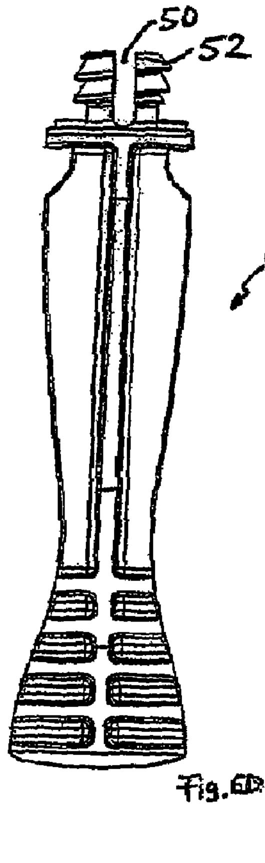
FIGS. 6C and 6D are schematic representations of the piston rod.
Figure 6C:
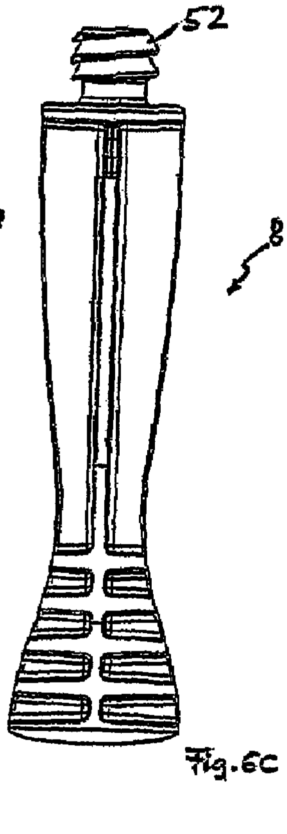

FIGS. 6C and 6D show schematic representations of the piston rod 46 without the piston stopper 42. The screw part 52 has a gap 50 which extends along the longitudinal axis and divides the screw part 52 into two parts. The two parts are resilient and may be pressed towards one another, for example when the piston stopper 42 is screwed on.

The external diameter of the screw part 52 is greater than the diameter of the female thread of the piston stopper 42 by a fixed amount. The resilience of the parts separated by the gap 50 compensates for the fixed difference of the diameters and manufacturing tolerances which might be present, i.e. the piston stopper 42 presses together the parts according to its female thread. The parts thus also press against the female thread of the piston stopper 42, whereby a zero clearance connection is produced and the piston rod 46 and the piston stopper 42 are held together in an improved way. This is an advantage when, at the end of the filling process, the patient taps with one finger against the wall of the ampoule 6 so that air bubbles which are possibly present in the ampoule 6 rise to the top.

This screw connection is thereby designed such that the torque for releasing the piston rod 46 is lower than the torque for rotating the piston stopper 42 in the ampoule 6. As a result, it is ensured that the piston rod 46 may be unscrewed without the piston stopper 42 rotating therewith.

The aforementioned embodiments of a system and a device for removing a pharmaceutical product from a reservoir 4 generally facilitate the removal or transfer of the pharmaceutical product. In the described embodiments, the filling of an empty ampoule 6 is primarily facilitated for the patient. The locking mechanism and the hollow spaces distributed on the ampoule increase the probability that, when coupling the ampoule 6 to the adaptor 2, the web 20 engages in a hollow space 40. For uncoupling, it is sufficient for the patient to pull on the adaptor 2 and/or on the ampoule 6, possibly with a rotary movement. The resilient web 20 then releases the collar part 32.

Further features which facilitate the operation or use of the present invention are the openings 18 and the slotted screw part 52. The openings 18 on the adaptor 2 facilitate the removal of undesired air from the ampoule 6 at the end of the filling process. As the patient thereby possibly taps the ampoule 6 and/or the piston rod 46, it is advantageous that the slotted screw part 52 sits firmly in the piston stopper 42 and is not inadvertently released.

While embodiments of the present invention have been described with reference to transferring or removing a substance from a reservoir to another container such as an ampoule, it should be appreciated that the adaptor and system according to the present invention could be used to transfer a substance from an ampoule to a reservoir as well. In some embodiments, the present invention comprises an adaptor and a system for facilitating the transfer of a substance from one container to another container, the adaptor comprising two connectors, one for coupling to one container and the other for coupling to the other container, wherein one of the connectors comprises a side wall with a peripheral area and a locking mechanism comprising a resilient element generally in the peripheral area and having opposing ends which merge with the side wall and the other connector comprises a side wall with an inner face with a bulged portion. A central part extends generally between the two connectors, and has at least one opening through which a portion of one of the containers is visible and at least one rib element extending radially outwardly.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An adaptor for facilitating the transfer of a substance from one container to another container, the adaptor comprising two connectors, one for coupling to the one container and the other for coupling to the another container, wherein one of the connectors comprises a side wall with a peripheral area and a releasable locking mechanism comprising a resilient element generally in the peripheral area, the resilient element having opposing ends which merge with the side wall, the resilient element resiliently deforming in a radial direction towards the side wall, the resilient element disposed circumferentially about the side wall.

2. The adaptor according to claim 1, wherein the locking mechanism comprises a slot, the resilient element extending generally parallel to the slot.

3. The adaptor according to claim 2, wherein the other connector comprises a side wall with an inner face with a bulged portion.

4. The adaptor according to claim 3, further comprising a central part extending generally between the two connectors, the central part comprising two opposing openings through which a portion of one of the containers is visible and at least one rib extending radially outwardly.

5. A system for transferring a substance, the system comprising an ampoule in which a moveable piston is arranged and an adaptor which has, longitudinally arranged, a reservoir connector and an ampoule connector for coupling to the ampoule, wherein the ampoule connector comprises a side wall and at least one releasable locking mechanism in the side wall configured to secure the ampoule, the locking mechanism comprising a resilient portion of the side wall extending along a portion of the periphery thereof, the resilient portion having opposed ends merging with the side wall, the resilient element resiliently deforming in a radial direction towards the side wall, the resilient element disposed circumferentially about the side wall.

6. A system for removing a pharmaceutical product from a reservoir with an ampoule in which a moveable piston is arranged and an adaptor which has, longitudinally arranged, a reservoir connector and an ampoule connector for coupling to the ampoule, wherein the ampoule connector has at least one releasable locking mechanism configured to secure the ampoule, which, in a side wall, comprises a resilient element corresponding to a portion of the side wall which extends along the periphery thereof, the resilient element having opposing ends merging with the side wall, the resilient element resiliently deforming in a radial direction towards the side wall, the resilient element disposed circumferentially about the side wall.

7. The system according to claim 6, the adaptor further comprising a central part between the reservoir connector and the ampoule connector and two opposing openings in the central part through which a front part of the ampoule is visible.

8. The system according to claim 6, the adaptor comprising a central part between the reservoir connector and the ampoule connector, the central part having at least one rib element which extends radially outwardly between the reservoir connector and the ampoule connector.

9. The system according to claim 6, the adaptor further comprising a central part between the reservoir connector and the ampoule connector, the central part comprising two opposing openings through which a front part of the ampoule is visible and at least one rib element which extends radially outwardly between the reservoir connector and the ampoule connector.

10. An adaptor system for removing a pharmaceutical product from a reservoir, the adaptor comprising a length and, longitudinally arranged, a reservoir connector and an ampoule connector for coupling to an ampoule, wherein the ampoule connector has at least one releasable locking mechanism configured to secure the ampoule, which, in a side wall, comprises a resilient element which corresponds to a portion of the side wall which extends along the periphery thereof, the resilient element having opposing ends merging with the side wall, the resilient element resiliently deforming in a radial direction towards the side wall, the resilient element disposed circumferentially about the side wall.

11. The adaptor according to claim 10, the adaptor further comprising a central part between the reservoir connector and the ampoule connector, the central part defining two opposing openings through which a front part of the ampoule is visible.

12. The adaptor according to claim 10, further comprising a central part between the reservoir connector and the ampoule connector and at least one rib element associated with the central part and extending radially outwardly between the reservoir connector and the ampoule connector.

13. The adaptor according to claim 10, further comprising a central part between the reservoir connector and the ampoule connector, the central part defining two opposing openings through which a front part of the ampoule is visible and carrying at least one rib element which extends radially outwardly between the reservoir connector and the ampoule connector.

14. The adaptor according to claim 13, wherein the at least one locking mechanism comprises a slot and wherein the resilient element extends parallel to the slot.

15. The adaptor according to claim 13, wherein the at least one locking mechanism comprises two slots and wherein the resilient element extends parallel to the slots.

16. The adaptor according to claim 10, wherein the reservoir connector has a non-circular cross-section.

17. The adaptor according to claim 10, wherein the reservoir connector has at least one recess in a side wall which produces a bulged portion on an inner face of the side wall.

* * * * *

UNITED STATES PATENT AND TRADEMARK OFFICE

CERTIFICATE OF CORRECTION

PATENT NO. : 8,187,248 B2
APPLICATION NO. : 12/207747
DATED : May 29, 2012
INVENTOR(S) : Rudolf Zihlmann It is certified that error appears in the above-identified patent and that said Letters Patent is hereby corrected as shown below:

Title Page;

(30) Foreign Application Priority Data

"(EP)..................06003098" should read --(EP).................06003098.8--.

Signed and Sealed this
Twenty-eighth Day of August, 2012

David J. Kappos

*Director of the United States Patent and Trademark Office*